US006316681B1

United States Patent
Yoshikawa et al.

(10) Patent No.: US 6,316,681 B1
(45) Date of Patent: Nov. 13, 2001

(54) METHOD FOR PRODUCING 1,1,1,3,3-PENTAFLUOROPROPANE

(75) Inventors: Satoshi Yoshikawa, Moroyama; Ryouichi Tamai, Kamifukuoka; Fuyuhiko Sakyu, Miyoshi; Yasuo Hibino, Shiki; Yoshihiko Gotoh, Miyoshi, all of (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 08/982,803

(22) Filed: Dec. 4, 1996

(30) Foreign Application Priority Data

Mar. 5, 1996 (JP) .................................... 8-047641
Apr. 3, 1996 (JP) .................................... 8-081557

(51) Int. Cl.⁷ .................................... C07C 17/08
(52) U.S. Cl. .................... 570/166; 570/168; 570/169
(58) Field of Search .................... 570/166, 168, 570/169

(56) References Cited

U.S. PATENT DOCUMENTS

| 2,787,646 | 4/1957 | Haszeldine . | |
|---|---|---|---|
| 2,942,036 | 6/1960 | Smith et al. . | |
| 5,616,819 | * 4/1997 | Boyce et al. | 570/166 |
| 5,710,352 | * 1/1998 | Tung | 570/166 |

FOREIGN PATENT DOCUMENTS 6-256235    9/1994   (JP) .

WO 96/017    1/1996   (WO) .

OTHER PUBLICATIONS

English translation of Izvestiya Akademii Nauk SSSR, Otdelenie Khimicheskikh Nauk, No.8, pp. 1412–1418, Aug. 1960 (CA 55,349f).
M. Kotora et al (1991) React.Kinet.Catal.Lett., vol. 44, No. 2, pp. 415–419.
M. Kotora et al. (1992) J.of Molecular Catalysis, vol. 77, pp. 51–60.
E.N. Zil'berman et al (1967) J. of Org.Chem. USSR, vol. 3, pp. 2101–2105.

* cited by examiner

*Primary Examiner*—Alan Siegel
(74) *Attorney, Agent, or Firm*—Crowell & Moring LLP

(57) ABSTRACT

The present invention relates to a method for producing 1,1,1,3,3-pentafluoropropane. This method includes a first step of fluorinating 1-chloro-3,3,3-trifluoropropene in a liquid phase by hydrogen fluoride in the presence of an antimony compound as a catalyst, or a second step of fluorinating 1-chloro-3,3,3-trifluoropropene in a gas phase by hydrogen fluoride in the presence of a fluorination catalyst. If the first step is taken, 1,1,1,3,3-pentafluoropropane can be produced with a high yield. If the second step is taken, 1,1,1,3,3-pentafluoropropane can continuously be easily produced. Therefore, the second step is useful for an industrial scale production thereof. According to the invention, 1-chloro-3,3,3-trifluoropropene may be produced by a method including a step of reacting 1,1,1,3,3-pentachloropropane with hydrogen fluoride in a gas phase in the presence of a fluorination catalyst. This method is useful, because yield of 1-chloro-3,3,3-trifluoropropene is high.

7 Claims, No Drawings

10

METHOD FOR PRODUCING 1,1,1,3,3-PENTAFLUOROPROPANE

BACKGROUND OF THE INVENTION

This invention relates to a method for producing 1,1,1,3,3-pentafluoropropane, which is useful as a foaming agent for foaming substances such as polyurethane, a refrigerant, and the like.

There are several conventional methods for producing 1,1,1,3,3-pentafluoropropane. For example, JP-A-Hei-6-256235 discloses a method for producing 1,1,1,3,3-pentafluoropropane from $CF_3$-$CClX$-$CF_2Cl$ where X is hydrogen or chlorine, by catalytic hydrogenation. A preferable catalyst for this method is a common hydrogenation catalyst. U.S. Pat. No. 2,942,036 discloses a method of hydrogenating 1,2,2-trichloropentafluoropropane to produce 1,1,1,3,3-pentafluoropropane or 1,1,3,3,3-pentafluoro-1-propane or mixtures thereof. A catalyst for this method is palladium carried on activated carbon. These two methods mentioned hereinabove are superior in conversion and selectivity. However, these catalysts deteriorate considerably in these methods. Furthermore, it is necessary to prepare the raw material(s) of these methods in advance. Thus, these methods may not be suitable for the production of 1,1,1,3,3-pentafluoropropane in an industrial scale.

There is disclosed, in published English translation (pp. 1312–1317) of Izvestiya Akademii Nauk SSSR, Otdelenie Khimicheskikh Nauk, No. 8, pp. 1412–1418, August, 1960 (CA 55, 349f), a method for producing 1,1,1,3,3-pentafluoropropane by hydrogenating 1,1,3,3,3-pentafluoro-1-propene in the presence of Pd-$Al_2O_3$. However, it is difficult to find the raw material of this method (i.e., 1,1,3,3,3-pentafluoro-1-propene) on the market.

There is another method for producing 1,1,1,3,3-pentafluoro-propane by fluorinating 1,1,1,3,3-pentachloropropane in a liquid phase in the presence of a catalyst (see WO96/01797). However, this method is relatively low in selectivity and yield.

Unlike 1,1,1,3,3-pentalfluoropropane mentioned hereinabove, there is known another compound, 1-chloro-3,3,3-trifluoropropene, which is useful as an intermediate of medicines, of agricultural chemicals, of functional materials, and of fluorohydrocarbons. This compound is obtained, for example, by the following first to fifth processes. In the first process, 1,1,1-trifluoropropane is chlorinated to obtain, 1,1,1-trifluoro-3,3-dichloropropane, and then this compound is dehydrochlorinated by an alcoholic basic compound to produce 1-chloro-3,3,3-trifluoropropene (see J. Am. Chem. Soc., 1942, 64, 1158). In the second process, hydrogen chloride is added to 3,3,3-trifluoropropyne to produce 1-chloro-3,3,3-trifluoropropene (see J. Chem. Soc., 1952, 3490). The second process is superior in conversion and selectivity. However, it is difficult to obtain the raw material of the second process (i.e., 3,3,3-trifluoropropyne) on the market. In the third process, 3-chloro-1,1,1-trifluoro,-3-iodopropane is dehydroiodinated by alcoholic potassium hydroxide to produce 1-chloro-3,3,3-trifluoropropene (see J. Chem. Soc., 1953, 1199). In the fourth process, 3-bromo-3-chloro-1,1,1-trifluoropropane is dehydrobrominated by an alcoholic potassium hydroxide (see R. N. Haszeldine, J. Chem. Soc., 15 1951, 2495). The third and fourth processes are superior in conversion and selectivity. However, according to these processes, there is needed more than stoichiometric amount of potassium hydroxide, and it is necessary to prepare the raw materials in advance. Thus, there are problems to apply these processes to an industrial scale production. In the fifth process, 1,3,3,3-tetrachloropropene is fluorinated by hydrogen fluoride in the presence of an antimony catalyst (see U.S. Pat. No. 2,787,646). In the fifth process, there are a problem that it is difficult to obtain the raw material of the reaction on the market, and another problem that the yield of 1-chloro-3,3,3-trifluoropropene is poor for the industrial scale production.

SUMMARY OF THE INVENTION

It is an object of the present invention to provide a method for producing 1,1,1,3,3-pentafluoropropane, which method is free of the above-mentioned drawbacks. It is a specific object of the present invention to provide a method for producing 1,1,1,3,3-pentafluoropropane with a high yield, which method is suitable for an industrial scale production.

It is another object of the present invention to provide a method for easily continuously producing 1,1,1,3,3-pentafluoropropane, in which method there is used a raw material of 1-chloro-3,3,3-trifluoropropene that can easily be obtained on the market.

According to a first aspect of the present invention, there is provided a first method for producing 1,1,1,3,3-pentafluoropropane, comprising a step of fluorinating 1-chloro-3,3,3-trifluoropropene in a liquid phase by hydrogen fluoride in the presence of an antimony compound as a catalyst. According to the first method, 1,1,1,3,3-pentafluoropropane can be produced with an high yield, due to the use of an antimony compound as a catalyst for the fluorination.

According to a second aspect of the present invention, there is provided a second method for producing 1,1,1,3,3-pentafluoropropane, comprising a step of fluorinating 1-chloro-3,3,3-trifluoropropene in a gas phase by hydrogen fluoride in the presence of a fluorination catalyst According to the second method, 1,1,1,3,3-pentafluoropropane can easily continuously be produced. Therefore, the second method is useful for an industrial scale production thereof. The raw material of the first and second methods, 1-chloro-3,3,3-trifluoropropene, can easily be obtained on the market.

According to the present invention, there is provided a third method for producing 1-chloro-3,3,3-trifluoropropene, which is a raw material of the first and second methods. The third method comprises a step of reacting 1,1,1,3,3-pentachloropropane with hydrogen fluoride in a gas phase in the presence of a fluorination catalyst. A raw material of the third method, 1,1,1,3,3-pentachloropropane, is easily obtained by one of the after-mentioned conventional methods. Furthermore, yield of 1-chloro-3,3,3-trifluoropropene is high, and therefore the third method is useful as an industrial-scale method for producing 1-chloro-3,3,3-trifluoropropene According to the present invention, the third method may be combined with either of the first and second methods, thereby to produce 1,1,1,3,3-pentafluoropropane from 1,1,1,3,3-pentachloropropane.

DESCRIPTION OF THE PREFERRED EMBODIMENTS

In accordance with the first aspect of the present invention, there will be described in detail the above-mentioned first method for producing 1,1,1,3,3-pentafluoropropane, as follows.

In the first method, the step may be conducted by a continuous operation, a batch operation, or a half-batch operation in which only the reaction product is continuously removed from a reactor. Hereinafter, the description of the first method will be concerned mainly with a batch operation. If the first method is conducted by another operation, it is optional to modify the reaction condition(s) of a batch operation, which will be described hereinafter.

It is known to use an antimony catalyst for fluorinating halogenated hydrocarbons in a liquid phase by hydrogen fluoride. It is generally assumed that this antimony catalyst under its activated condition during the fluorination takes a form of a halogenated antimony compound represented by a formula of $SbF_aX_b$ where X is a halogen, "a" and "b" are numbers each ranging from 0 to 5, and the total of "a" and "b" equals to 5. Thus, it is assumed that an antimony compound used as a catalyst in the first method also takes a form of such halogenated antimony compound, regardless of the form of the original antimony compound, when the antimony compound is under its activated condition during the fluorination. A halogenated antimony(III) compound, which is in a non-activated condition, is easily oxidized to another halogenated antimony(V) compound, which is in an activated condition, by chlorine, bromine or fluorine. Therefore, an antimony compound that is introduced as a catalyst into the reaction system of the first method is not limited to an antimony(V) compound. Examples of an antimony compound used in the first method are antimony pentachloride, antimony pentabromide, antimony pentaiodide, antimony pentafluoride, antimony trichloride, antimony tribromide, antimony triiodide, and antimony trifluoride. Of these, antimony pentachloride and antimony trichloride are particularly preferable examples.

In the first method, the catalyst is in an amount of preferably from 0.1 to 50 moles, more preferably from 10 to 30 moles, per 100 moles of 1-chloro-3,3,3-trifluoropropene. If it is less than 0.1 moles, both of conversion of 1-chloro-3,3,3-trifluoropropene and yield of 1,1,1,3,3-pentafluoropropane may become too low. If it is greater than 50 moles, tarry substances made up of high-boiling-point compounds may be produced too much.

In the first method, the reaction temperature is preferably from 10 to 150° C., more preferably from 50 to 130°C. If it is lower than 10°C., both of conversion of 1-chloro-3,3,3-trifluoropropene and yield of 1,1,1,3,3-pentafluoropropane may become too low. If it is higher than 150° C., tarry substances may be produced too much, and the catalyst may deteriorate considerably.

In the first method, the molar ratio of hydrogen fluoride to 1-chloro-3,3,3-trifluoropropene is preferably from 2:1 to 30:1, more preferably from 3:1 to 20:1. If it is less than 2:1, conversion of 1-chloro-3,3,3-trifluoropropene may not become sufficiently high. If it is greater than 30:1, conversion of 1-chloro-3,3,3-trifluoropropene may not improve further, as compared with a case in which it is within this range of from 2:1 to 30:1. Furthermore, this may not economically be advantageous from the viewpoint of the recovery of the unreacted hydrogen fluoride.

In the first method, pressure needed to conduct the fluorination varies depending on the reaction temperature, and this pressure is not particularly limited as long as the reaction mixture in the reactor is maintained in the form of liquid. The pressure is preferably from 1.0 to 100 kg/cm$^2$, more preferably from 5 to 30 kg/cm$^2$.

In the first method, a solvent may be added to the reaction system in order to adjust the reaction rate and to suppress deterioration of the catalyst. Preferable examples of this solvent are 1,1,1,3,3-pentafluoropropane, which is the aimed product, and polychlorinated compounds (e.g., tetrachloroethane), which are hardly further chlorinated while the deteriorated catalyst is activated.

When the catalyst of the first method has deteriorated or has been an antimony compound that has an antimony's oxidation number other than +5, this catalyst can easily be activated to an activated condition where its antimony has an oxidation number of +5. This activation is conducted by introducing chlorine into the reaction system at a temperature of from 10 to 100° C., in the presence of a solvent such as 1-chloro-3,3,3-trifluoropropene, 1,1,1,3,3-pentafluoropropane or the above-mentioned polychlorinated compound. Upon or after the introduction, stirring is conducted, if necessary. For the activation, chlorine is used in an amount of from 1 to 100 moles per mol of the catalyst. If the temperature is lower than 10° C., it takes too long time to achieve the activation. If it is higher than 100° C., the coexisting 1-chloro-3,3,3-trifluoropropene, 1,1,1,3,3-pentafluoropropane and/or polychlorinated compound may be chlorinated.

A reactor used in the first method is preferably made of a material such as Hastelloy, stainless steel, Monel metal or nickel, or a material lined with one of these metals, tetrafluoroethylene resin, chlorotrifluoroethylene resin, vinylidene fluoride resin or PFA resin.

In the first method, the obtained 1,1,1,3,3-pentafluoropropane may be purified by a conventional method for purifying reaction products obtained by the fluorination. In this purification, for example, 1,1,1,3,3-pentafluoropropane, together with hydrogen chloride and the unreacted hydrogen fluoride, is discharged in the form of liquid or gas, from a reactor. Then, an excessive amount of hydrogen fluoride is removed from the discharge by the liquid phase separation or the like. Then, an acid component is removed therefrom using water or a basic solution. After that, the aimed 1,1,1,3,3-pentafluoropropane having a high purity is obtained by distillation.

In the following, there will be described in detail the above-mentioned second method for producing 1,1,1,3,3-pentafluoropropane, in accordance with the second aspect of the present invention. Furthermore, there will be described in detail the above-mentioned third method for producing 1-chloro-3,3,3-trifluoropropene, which is used as a raw material in each of the first and second methods, as follows. In the invention, as stated above, 1,1,1,3,3-pentafluoropropane may be produced from 1,1,1,3,3-pentachloropropane, by combining the third method with either of the first and second methods.

As stated above, the second method comprises a step of fluorinating 1-chloro-3,3,3-trifluoropropene in a gas phase by hydrogen fluoride in the presence of a fluorination catalyst. The third method comprises a step of reacting 1,1,1,3,3-pentachloropropane with hydrogen fluoride in a gas phase in the presence of a fluorination catalyst.

A raw material of the third method, 1,1,1,3,3-pentachloropropane, may be produced, for example, by the following conventional first, second, and third processes. In the first process, vinylidene chloride is reacted with chloroform in the presence of copper-amine catalyst (see M. Kotora et al. (1991) React. Kinet. Catal. Lett., Vol. 44, No. 2, pp. 415–419). In the second process, carbon tetrachloride is reacted with vinyl chloride in the presence of copper-amine catalyst (see M. Kotora et al. (1992) J. of Molecular Catalysis, Vol. 77, pp. 51–60). In the third process, carbon tetrachloride is reacted with vinyl chloride in an isopropanol solvent, in the presence of a ferrous chloride catalyst (see E. N. Zil'berman et al. (1969) J. of Org. Chem. USSR, Vol. 3, pp. 2101–2105).

The fluorination catalyst used in each of the second and third methods has a first preferable example that is at least one compound of at least one metal selected from the group consisting of aluminum, chromium, manganese, nickel, and cobalt. Hereinafter, this example will be referred to as the first fluorination catalyst. In the second method, when a combination of at least two compounds of at least two metals is used for preparing the first fluorination catalyst, the at least two metals preferably include chromium. Examples of the at least one compound of the first fluorination catalyst are oxide, fluoride, chloride, fluorochloride, oxyfluoride, oxychloride, and oxyfluorochloride. The at least one compound may be carried on a carrier such as an aluminum compound or activated carbon. Examples of this aluminum compound are aluminum oxide, fluoride, chloride, fluorochloride, oxyfluoride, oxychloride, and oxyfluorochloride.

In each of the second and third methods, the manner of preparing the first fluorination catalyst is not particularly limited. When the at least one compound is not carried on a carrier, the at least one compound may be prepared, as follows. At first, a metal hydroxide is precipitated from a solution of a compound of the at least one metal, using a basic substance. After that, this metal hydroxide is turned into a metal oxide, and then this metal oxide is partially or completely modified by halogen, using hydrogen fluoride, hydrogen chloride, chlorofluorohydrocarbon, and the like. In contrast, when the at least one compound is carried on a carrier, the carrier may be immersed into a solution of the at least one compound, or alternatively this solution may be sprayed on the carrier. The carrier may be, for example, an aluminum oxide such as γ-alumina or an alumina that has previously been modified by hydrogen fluoride, hydrogen chloride, chlorofluorohydrocarbon or the like.

In each of the second and third methods, the amount of the at least one metal of the first fluorination catalyst is preferably from 0.1 to 20 wt % and more preferably from 1 to 10 wt %, based on the total weight of the carrier. It is optional to add an additive that is at least one element of alkali-earth metals such as Mg and Ca and lanthanide series elements such as La and Ce, to the first fluorination catalyst. This additive prevents recrystallization of an oxyhalide used as the at least one metal or as the carrier, thereby maintaining activity of the first fluorination catalyst. Weight ratio of the at least one metal to the additive is preferably from 50:50 to 99.9:0.1 and more preferably from 70:30 to 99:1.

In each of the second and third methods, at least one metal compound used for preparing the first fluorination catalyst may be at least one of nitrate, chloride, oxide and the like of the at least one metal, which is soluble in a solvent such as water, ethanol, or acetone. Examples of the at least one metal compound are chromium nitrate, chromium trichloride, chromium trioxide, potassium dichromate, manganese nitrate, manganese chloride, manganese dioxide, nickel nitrate, nickel chloride, cobalt nitrate, and cobalt chloride.

Only in the third method, the fluorination catalyst has further second and third preferable examples that are respectively a partially fluorinated aluminum oxide and a stainless steel that has been treated with hydrogen fluoride. Hereinafter, these preferable examples will respectively be referred to as the second and third fluorination catalysts. Aluminum oxide has various morphologies depending on the manner of preparing the same. Aluminum oxide used in the third method is not limited to a particular type, and γ-alumina can easily be found on the market and thus is preferably used for that. Of γ-alumina, there is preferably used in the third method an activated alumina that is generally used for supporting catalyst, that is relatively large in specific surface area, and that is superior in heat resistance. Examples of stainless steel used in the third method are ferrite-type stainless steel (SUS 430) and austenite-type stainless steels (SUS 304, 304L, 316, and 316L). Preferable examples of the same are stainless steels that are in the forms of wool, net, wire and thin tube, and a distillation tower's filler that is prepared from one of these stainless steels into an arbitrary shape.

In the third method, the manner of preparing the second and third fluorination catalysts is not particularly limited. The second fluorination catalyst may be prepared by sequential steps of (a) preparing aluminum oxide from the precursor in the form of sphere or rod; and (b) treating the aluminum oxide with a fluorine-containing compound by spraying of a hydrofluoric acid solution, by immersion into this solution, or by bringing the aluminum oxide into contact with a gas that is hydrogen fluoride, fluorohydrocarbon or chlorofluorohydrocarbon under an elevated temperature. The third fluorination catalyst is prepared by immersing stainless steel into a hydrofluoric acid solution, followed by drying, or by filling a reaction tube with stainless steel and then allowing hydrogen fluoride to flow through the reaction tube.

In each of the second and third method, compositional change of the fluorination catalyst during the fluorination can effectively be prevented by treating, prior to the fluorination, the fluorination catalyst with a fluorination agent such as hydrogen fluoride, fluorohydrocarbon or fluorochlorohydrocarbon, at a temperature not lower than the reaction temperature of the fluorination. The fluorination catalyst can effectively be prolonged in lifetime, and furthermore conversion and yield of the fluorination can effectively be improved, by supplying the reactor with oxygen, chlorine, fluorohydrocarbon or fluorochlorohydrocarbon, during he fluorination.

In the second method, the reaction temperature is preferably from 100 to 500° C., more preferably from 200 to 400° C. If the reaction temperature is too low, the reaction rate may become impractically slow. If the reaction temperature is too high, the reaction rate becomes high. With this, however, there may be produced an olefin(s) such as tetrafluoropropene, and thus selectivity of 1,1,1,3,3-pentafluoropropane may be lowered.

In the third method, when the first fluorination catalyst is used, the reaction temperature is preferably from 100 to 450° C. and more preferably from 150 to 300° C. When either of the second and third fluorination catalysts is used, the reaction temperature is preferably from 100 to 500° C. and more preferably from 200 to 400° C. If the reaction temperature is too low, the reaction rate may become impractically slow. If the reaction temperature is too high, the reaction rate becomes high. With this, however, the fluorination catalyst may become short in lifetime. Furthermore, the amount of undesirable by-products such as olefins may increase, and thus selectivity of 1-chloro-3,3,3-trifluoropropene may be lowered.

In the second and third methods, the ratio by mol of 1-chloro-3,3,3-trifluoropropene to hydrogen fluoride and that of 1,1,1,3,3-pentachloropropane to hydrogen fluoride respectively vary depending on the reaction temperature. This ratio of the second method is preferably from 1/80 to 1/2, more preferably from 1/40 to 1/3. In order to obtain a high reaction rate, it is preferred that the concentration of hydrogen fluoride is high in the reaction system, because it is assumed that an equilibrium state exists among 1,1,1,3, 3-pentafluoropropane, its precursors, hydrogen fluoride and hydrogen chloride. This ratio of the third method is preferably from 1/30 to 1/3, more preferably from 1/10 to 1/3. If the amount of hydrogen fluoride is too large in each of the second and third methods, the amount of the reaction product contained in the unit volume of the gas released from the reactor may become small. Furthermore, it may become difficult to separate the reaction product from a mixture of the reaction products and the unreacted hydrogen fluoride released from the reactor. If the amount of hydrogen fluoride is too small in each of the second and third methods, conversion may become low, thereby lowering yield of the reaction product. However, even if the amount of hydrogen fluoride is too much or too little in each of the second and third methods, that is not critical to the fluorination of large scale, because low-fluorinated compounds, unreacted substances, and/or hydrogen fluoride, which usually accompanies the reaction product, is separated from the reaction product and is reused.

In each of the second and third methods, the reaction pressure is not particularly limited. It is preferably from 1 to 10 kg/cm$^2$ from the viewpoint of the selection of the reactor material. In each of these methods, it is preferable to select a reaction condition in which the hydrocarbon (i.e., 1-chloro-3,3,3-trifluoropropene or 1,1,1,3,3-pentachloropropane) used as the raw material, intermediate products and hydrogen fluoride, which exist in the reaction system, are not liquefied in the reaction system. In each of these methods, the contact time of the fluorination is preferably from 0.1 to 300 seconds. In the second method, it is more preferably from 5 to 60 seconds. In the third method, when the first fluorination catalyst is used, it is more preferably from 5 to 100 seconds; and, when either of the second and third fluorination catalysts is used, it is more preferably from 5 to 60 seconds.

The reactor's material used in each of the second and third methods is not particularly limited, as long as the reactor has a sufficient heat resistance and a sufficient corrosion resistance against hydrogen fluoride, hydrogen chloride and the like. It is preferably stainless steel, Hastelloy, Monel metal or platinum, or a material lined with one of these metals.

In each of the second and third methods, the reaction products containing 1-chloro-3,3,3-trifluoropropene or 1,1,1,3,3-pentafluoropropane may be purified by a conventional purification process that is not particularly limited. In this process, for example, the reaction products are washed with water and/or an aqueous basic solution to remove acid substances such as hydrogen chloride and hydrogen fluoride. Then, the washed reaction products are dried and then distilled to remove organic impurities.

The first aspect of the present invention will be illustrated with reference to the following nonlimitative Examples 1–2.

EXAMPLE 1

In this example, 1,1,1,3,3-pentafluoropropane was prepared from 1-chloro-3,3,3-trifluoropropene, as follows, in accordance with the first method of the present invention.

At first, 0.053 mol (15.9 g) of antimony pentachloride (catalyst), 5.0 mol (100 g) of hydrogen fluoride, and 0.265 mol (34.6 g) of 1-chloro-3,3,3-trifluoropropene were introduced into a 1-liter autoclave made of stainless steel (SUS 316L) and equipped with a reflux condenser and a stirrer. Then, the autoclave's temperature was increased to 71° C., while the reaction mixture was stirred. During the reaction, the autoclave's temperature was maintained within a range of from 71 to 74° C. As the reaction proceeded, the autoclave's inside pressure increased due to the generation of hydrogen chloride. When the pressure reached 10 kg/cm$^2$, it was started to remove hydrogen chloride from the autoclave through the reflux condenser in order to maintain the reaction pressure at 10 kg/cm$^2$ during the reaction. Three hours after the beginning of the reaction, the autoclave was cooled down to room temperature. Then, the effluent (gas) was discharged from the autoclave by reducing the autoclave's inside pressure to atmospheric pressure. Then, the effluent was allowed to flow through a water layer and then was condensed and collected in a trap that was previously cooled down by dry ice and methanol. The combined products composed of the thus collected matter and the content of the autoclave were washed with hydrochloric acid and then with water. With this, 28.7 g of an organic matter was obtained as a whole. By analysis with a gas chromatograph, it was found that this organic matter contains 93.9 mol % of 1,1,1,3,3-pentafluoropropane, 2.7 mol % of 3,3,3-trifluoro-1-chloro-1-propene, 1.4 mol % of 1,1,1,3-tetrafluoro-3-chloro-1-propane, and 2.0 mol % of high-boiling-point substances.

EXAMPLE 2

In this example, 1,1,1,3,3-pentafluoropropane was prepared from 1-chloro-3,3,3-trifluoropropene, as follows, in accordance with the first method of the present invention.

At first, 0.1 mol (29.9 g) of antimony pentachloride (catalyst), 5.0 mol (100 g) of hydrogen fluoride, 0.3 mol (50.4 g) of 1,1,2,2-tetrachloroethane, and 1.0 mol (130.5 g) of 1-chloro-3,3,3-trifluoropropene were introduced into a 1-liter autoclave that is the same as that of Example 1. Then, the autoclave's temperature was increased to 65° C., while the reaction mixture was stirred. During the reaction, the autoclave's temperature was maintained within a range of from 65 to 70° C. A the reaction proceeded, the autoclave's inside pressure increased due to the generation of hydrogen chloride. When the pressure reached 8.5 kg/cm$^2$, it was started to remove hydrogen chloride from the autoclave through the reflux condenser in order to maintain the reaction pressure at 8.5 kg/cm$^2$ during the reaction. The reaction was conducted for the same period of time as that of Example 1. After that, the reaction products were collected and then washed in the same manner as that of Example 1. With this, 149 g of an organic matter was obtained as a whole. By analysis with a gas chromatograph, it was found that this organic matter contains 98.3 mol % of 1,1,1,3,3-pentafluoropropane, 0.1 mol % of 3,3,3-trifluoro-1-chloro-1-propene, 1.1 mol % of 1,1,1,3-tetrafluoro-3-chloropropane, and 0.5 mol % of high-boiling-point substances. Although the organic matter contained 35% of a solvent, the solvent was excluded from the results of chemical composition of the organic matter.

The second aspect of the present invention will be illustrated with reference to the following nonlimitative Examples 3, 3A, 4, and 4A.

EXAMPLE 3

In this example, 1,1,1,3,3-pentafluoropropane was produced by fluorinating 1-chloro-3,3,3-trifluoropropene with hydrogen fluoride in a gas phase in the presence of the first fluorination catalyst, as follows.

The first fluorination catalyst was prepared as follows. At first, 1 liter of a CrCl$_3$ aqueous solution was prepared by dissolving 336 g of CrCl$_3$6H$_2$O into pure water. Into this solution, there was immersed 250 cc of an activated alumina in the form of sphere that is made by SUMITOMO CHEMICAL CO., LTD. and has a trade name of NKH3-24, a diameter of from 2 to 4 mm, a specifc surface area of 340 m²/g and a morphological property of γ-alumina, and then this solution was allowed to stand still for one day and one night. After that, the activated alumina was separated from the solution by filtration, and then was dried for one day and one night at 100° C. in a hot-air circulating type oven. The thus obtained chromium-carried alumina was put into a cylindrical reaction tube that is equipped with an electric furnace and is made of stainless steel (SUS316L) and has a diameter of 5 cm and an axial length of 30 cm. The reaction tube temperature was increased to 300° C., while nitrogen gas was allowed to flow therethrough. Then, at the time when a trace of water was not found in the exit gas, it was started to allow hydrogen fluoride to flow therethrough, together with nitrogen gas. Then, hydrogen fluoride concentration of the mixture of hydrogen fluoride and nitrogen was gradually increased. When a hot spot produced by fluorinating the chromium-carried alumina reached the end of exit of the reaction tube, the reaction tube temperature was further increased to 450° C. Then, this condition was maintained for 1 hr, thereby preparing the first fluorination catalyst.

Then, the fluorination was conducted as follows. At first, a cylindrical reaction tube for conducting a gas phase reaction was charged with 150 cc of the above-prepared first fluorination catalyst. This reaction tube was equipped with an electric furnace and was made of stainless steel (SUS316L) and had a diameter of 1 inch and an axial length of 30 cm. Then, the reaction tube temperature was increased to 450° C., while nitrogen gas was allowed to flow therethrough at a flow rate of about 135 cc/min. Then, hydrogen fluoride gas was also allowed to flow therethrough at a flow rate of about 0.35 g /min, together with nitrogen gas. Then, the reaction tube temperature was lowered to 350° C., and then this condition was maintained for 1 hr. Then, the reaction tube temperature was decreased to 300° C., and then the reaction (fluorination) was started by supplying the reaction Tube with 1-chloro-3,3,3-trifluoropropene that had previously been vaporized, at a flow rate of 0.21 g/min, with nitrogen gas at a flow rate of 60 cc/min and with hydrogen fluoride at a flow rate of 0.13 g/min. 1 hr after the start of the reaction, the reaction became stationary. After that, the reaction products (gas) were bubbled for 1 hr into water to remove an acid gas therefrom and then were collected by a trap cooled in dry ice and acetone. With this, 11.9 g of an organic matter was obtained. This organic matter was analyzed with a gas chromatograph. With this analysis, it was found that the organic matter contains 93.6% of 1-chloro-3,3,3-trifluoropropene, 6.3% of 1,1,1,3,3-pentafluoropropane, and 0.1% of 1,3,3,3-tetrafluoropropene.

EXAMPLE 3A

In this example, Example 3 was modified, as follows.

The first fluorination catalyst was prepared as follows. At first, 1 liter of a CrCl₃ aqueous solution was prepared by dissolving 200 g of CrCl₃6H₂O into pure water. Into this solution, there was immersed 300 cc of an activated carbon, which is made by TOYO CALGON CO., LTD. and has a trade name of PCB and a size of 6×6 mesh, and then this solution was allowed to stand still for one day and one night. After that, the activated carbon was separated from the solution by filtration, and then was dried for one day and one night at 150° C. in a hot-air circulating type oven. The thus obtained chromium-carried activated carbon was put into a cylindrical reaction tube that is equipped with an electric furnace and is made of stainless steel (SUS316L) and has a diameter of 5 cm and an axial length of 30 cm. The reaction tube temperature was increased to 300° C., while nitrogen gas was allowed to flow therethrough. Then, at the time when a trace of water was not found in the exit gas, it was started to allow hydrogen fluoride to flow therethrough, together with nitrogen gas. Then, hydrogen fluoride concentration of the mixture of hydrogen fluoride and nitrogen was gradually increased. When a hot spot produced by the treatment reached the end of exit of the reaction tube, the reaction tube temperature was further increased to 400° C. Then, this condition was maintained for 1 hr, thereby preparing the first fluorination catalyst.

Then, the fluorination was conducted as follows. At first, a cylindrical reaction tube for conducting a gas phase reaction was charged with 150 cc of the above-prepared first fluorination catalyst. This reaction tube was equipped with an electric furnace and was made of stainless steel (SUS316L) and had a diameter of 1 inch and an anal length of 30 cm. Then, the reaction tube temperature was increased to 400° C., while nitrogen gas was allowed to flow therethrough at a flow rate of about 135 cc/min. Then, hydrogen fluoride gas was also allowed to flow therethrough at a flow rate of about 0.30 g /min, together with nitrogen gas. Then, the reaction tube temperature was lowered to 300° C., and then this condition was maintained for 1 hr. Then, the reaction tube temperature was decreased to 280° C., and then the reaction (fluorination) was started by supplying the reaction tube with 1-chloro-3,3,3-trifluoropropene that had previously been vaporized, at a flow rate of 0.05 g/min, with nitrogen gas is at a flow rate of 30 cc/min and with hydrogen fluoride at a flow rate of 0.30 g/min. 6 hr after the start of the reaction, the reaction became stationary.

After that, the reaction products (gas) were bubbled for 1 hr into water to remove an acid gas therefrom and then were collected by a trap cooled in dry ice and acetone. With this, 16.0 g of an organic matter was obtained. This organic matter was analyzed with a gas chromatograph. With this analysis, it was found that the organic matter contains 26.3% of 1-chloro-3,3,3-trifluoropropene, 54.6% of 1,1,1,3,3-pentafluoropropane, and 18.2% of 1,3,3,3-tetrafluoropropene.

EXAMPLE 4

In this example, Example 3 was repeated except in that the reaction tube temperature was maintained for 1 hr at 450° C. in place of 350° C., without lowering the reaction tube temperature from 450° C. to 350° C., and that the reaction was conducted at 450° C. in place of 300° C., without changing the reaction tube temperature after maintaining the same at 450° C. for 1 hr. With this, 11.6 g of an organic matter was obtained. By an analysis with a gas chromatograph, it was found that the organic matter contains 64.1% of 1-chloro-3,3,3-trifluoropropene, 35.4% of 1,1,1,3,3-pentafluoropropane, and 0.5% of 1,3,3,3-tetrafluoropropene.

EXAMPLE 4A

In this example, Example 3A was repeated except in that the reaction products in Example 3A was used as an organic starting material in place of 1-chloro-3,3,3-trifluoropropane, and that the reaction was conducted at 250° C. in place of 280° C., and that the flow rate of hydrogen fluoride was adjusted so that the molar ratio of hydrogen fluoride to the organic starting material was 30 to 1With this, 13.8 g of an organic matter was obtained. By an analysis with a gas chromatograph, it was found that the organic matter contains 5.5% of 1-chloro-3,3,3-trifluoropropene, 78.4% of 1,1,1,3, 3-pentafluoropropane, and 15.9% of 1,3,3,3-tetrafluoropropene

EXAMPLE 5

In this example, 1-chloro-3,3,3-trifluoropropene was produced by fluorinating 1,1,1,3,3-pentachloropropane with hydrogen fluoride in a gas phase in the presence of the first fluorination catalyst, as follows.

The first fluorination catalyst was prepared in the same manner as that of Example 3, except in that the reaction tube temperature was increased to and maintained for 1 hr at 350° C., in place of 450° C.

Then, the fluorination was conducted as follows. At first, 50 cc of the above-prepared first fluorination catalyst was put into a cylindrical reaction tube that is the same as that of Example 3. Then, the reaction tube temperature was increased to 300° C., while nitrogen gas was allowed to flow therethrough at a flow rate of about 190 cc/min. Then, hydrogen fluoride gas was also allowed to flow therethrough at a flow rate of about 0.25 g /min, together with nitrogen gas. Then, the reaction tube temperature was increased to 350° C., and then this condition was maintained for 1 hr. Then, the reaction tube temperature was decreased to 220° C., and then the reaction (fluorination) was started by supplying the reaction tube with 1,1,1,3,3-pentachloropropane that had previously been vaporized, at a flow rate of 0.35 g/min, and with hydrogen fluoride at a flow rate of 0.29 g /min, as shown in Table 1. 1 hr after the start of the reaction, the reaction became stationary. After that, the reaction products were collected in a manner that is the same as that of Example 3. The organic matter obtained above was analyzed with a gas chromatograph, and the results of this analysis are shown in Table 2.

TABLE 1

| | Reaction Temp. (°C.) | Reactants Flow Rates (g/min) | |
|---|---|---|---|
| | | 1,1,1,3,3-pentachloropropane | Hydrogen Fluoride |
| Example 5 | 220 | 0.35 | 0.29 |
| Example 6 | 200 | 0.30 | 0.25 |
| Example 7 | 150 | 0.27 | 0.24 |
| Example 8 | 300 | 0.28 | 0.27 |

TABLE 2

| | Nitrogen Gas Flow Rate (ml/min) | Yield of 1-chloro-3,3,3-trifluoropropene (%) | Purity of 1-chloro-3,3,3-trifluoropropene (%) |
|---|---|---|---|
| Example 5 | 190 | 95 | 97 |
| Example 6 | 170 | 86 | 97 |
| Example 7 | 185 | 82 | 86 |
| Example 8 | 185 | 84 | 84 |

EXAMLPES 6–8

In these examples, Example 5 was repeated except in that the reaction conditions were modified as shown in Tables 1–2.

EXAMPLE 9

In this example, 1-chloro-3,3,3-trifluoropropene was produced by reaction 1,1,1,3,3-pentachloropropane with hydrogen fluoride in a gas phase in the presence of the second fluorination catalyst, as follows.

The second fluorination catalyst was prepared as follows. At first, 300 g of the activated alumina having a trade name of NKH3-24 was washed with water to remove a powder attached to the surface of the activated alumina. Separately, 10% hydrofluoric acid solution was prepared by dissolving 115 g of anhydrous hydrogen fluoride into 1,035 g of water. Then, the hydrofluoric acid solution was gradually poured on the activated alumina. After stirring, this mixture was allowed to stand still for 3 hr. After that, the activated alumina separated from the solution was washed with water, then was separated from water by filtration, and then was dried at 200° C. for 2 hr in an electric furnace. Then, 150 cc of the dried activated alumina was put into a stainless steel reaction tube having an inner diameter of 1 inch and an axial length of 30 cm. Then, this reaction tube was put into the electric furnace, and then the electric furnace temperature was increased to 200° C., while nitrogen gas was allowed to flow through the reaction tube. After that, hydrogen fluoride gas together with nitrogen gas was allowed to flow therethrough to treat the active aluminum with hydrogen fluoride. As this treatment proceeded, the temperature of catalyst increased. In this treatment, flow rates of nitrogen and hydrogen fluoride were respectively adjusted such that the temperature of catalyst did not exceed 400° C. After this exothermic reaction of the active aluminum with hydrogen fluoride has finished, the reaction tube was further kept in the electric furnace at 400° C. for 2 hr.

Then, a cylindrical reaction tube for conducting a gas phase reaction was charged with 150 cc of the above-treated active aluminum. This reaction tube was equipped with an electric furnace and was made of stainless steel (SUS316L) and had a diameter of 1 inch and an axial length of 30 cm. The reaction tube temperature was increased to 300° C., while nitrogen gas was allowed to flow therethrough at a flow rate of about 160 cc/min. After the temperature rose to 300° C., hydrogen fluoride gas was allowed to flow therethrough at a flow rate of about 0.20 g/min, together with nitrogen gas. Under this condition, the reaction tube temperature was increased to a maximum temperature of 350° C. and then was maintained at this temperature for 1 hr. Then, the reaction tube temperature was lowered to 250° C., and then the reaction (fluorination) was started by supplying the reaction tube with 1,1,1,3,3-pentachloropropane that had previously been vaporized, at a flow rate of 0.27 g/min, as shown in Table 3. One hr after the start of the reaction, the reaction became stable. After that, the reaction products (gas) released from the reaction tube were bubbled into water to remove an acid gas therefrom and then were collected by a trap cooled in dry ice and acetone. With this, 17.8 g of an organic matter was obtained. This organic matter was analyzed with a gas chromatograph, and the results of this analysis are shown in Table 4. In each of this example and the after-mentioned Examples 10–18, the rest of the organic matter, except 1,3,3,3-tetrafluoropropene, 1,1 1,3,3-pentafluoropropane and 1-chloro-3,3,3-trifluoropropene which are mentioned in Table 4, was an substance(s).

TABLE 3

| | Reaction Temp. (° C.) | Reactants Flow Rates (g/min) | |
|---|---|---|---|
| | | 1,1,1,3,3-pentachloropropane | Hydrogen Fluoride |
| Example 9 | 250 | 0.27 | 0.20 |
| Example 10 | 250 | 0.56 | 0.19 |

TABLE 3-continued

| | Reaction Temp. (° C.) | Reactants Flow Rates (g/min) 1,1,1,3,3-pentachloropropane | Hydrogen Fluoride |
|---|---|---|---|
| Example 11 | 300 | 0.56 | 0.19 |
| Example 12 | 350 | 0.56 | 0.19 |
| Example 13 | 400 | 0.56 | 0.19 |
| Example 14 | 250 | 1.01 | 0.40 |
| Example 15 | 300 | 1.01 | 0.40 |
| Example 16 | 250 | 1.01 | 0.40 |
| Example 17 | 300 | 1.01 | 0.40 |
| Example 18 | 350 | 1.01 | 0.40 |

TABLE 4

| | Reaction Products Weight (g) | Chemical Composition of Reaction Products (mol %) | | |
|---|---|---|---|---|
| | | 1,3,3,3-tetrafluoro-propropene | 1,1,1,3,3-pentafluoro-propane | 1-chloro-3,3,3-trifluoro-propene |
| Example 9  | 17.8 | 1.2 | 0.9 | 96.1 |
| Example 10 | 38.0 | 0.2 | 0.1 | 97.3 |
| Example 11 | 37.4 | 1.0 | 0.4 | 96.7 |
| Example 12 | 37.7 | 1.0 | 0.2 | 96.7 |
| Example 13 | 36.1 | 1.5 | 0.3 | 94.2 |
| Example 14 | 67.2 | 0.4 | 0.1 | 87.2 |
| Example 15 | 66.4 | 0.8 | 0.2 | 97.2 |
| Example 16 | 66.2 | 0.5 | 0.3 | 97.2 |
| Example 17 | 65.4 | 0.9 | 0.2 | 97.5 |
| Example 18 | 64.4 | 1.2 | 0.6 | 96.2 |

EXAMPLES 10–13

In these examples, Example 9 was repeated except in that the reaction conditions were modified as shown in Table 3. Only in Example 13, however, the reaction tube temperature was increased to a maximum of 400° C., in place of 350° C.

EXAMPLES 14–15

In these examples, Example 9 was repeated except in that the reaction conditions were modified as shown in Table 3 and that the nitrogen gas flow rate was modified into 320 cc/min.

EXAMPLE 16

In this example, 1-chloro-3,3,3-trifluoropropene was produced by fluorinating 1,1,1,3,3-pentachloropropane with hydrogen fluoride in a gas phase in the presence of the third fluorination catalyst, as follows.

The third fluorination catalyst was prepared as follows. At first, 150 cc of pole rings each having a diameter of 5 mm and an axial length of 6 mm, which are used for a distillation tower and are made of stainless steel (SUS316L), was put into a stainless steel reaction tube having an inner diameter of 1 inch and an axial length of 30 cm. Then, this reaction tube was put into the electric furnace, and the electric furnace temperature was increased to 200° C., while nitrogen gas was allowed to flow through the reaction tube. After that, hydrogen fluoride gas together with nitrogen gas was allowed to flow therethrough to treat the pole rings with hydrogen fluoride. In this treatment, flow rates of nitrogen and hydrogen fluoride were respectively adjusted for 2 hr such that the furnace temperature did not exceed 400° C. With this, the third fluorination catalyst was prepared.

Then, a cylindrical reaction tube that is the same as that of Example 9 was charged with 150 cc of the above-prepared third fluorination catalyst. The reaction tube temperature was increased to 300° C., while nitrogen gas was allowed to flow therethrough at a flow rate of about 320 cc/min. Then, hydrogen fluoride gas was allowed to flow therethrough at a flow rate of about 0.40 g/min, together with nitrogen gas. Under this condition, the reaction tube temperature was increased to a maximum temperature of 350° C. and then was maintained at this temperature for 1 hr. Then, the reaction tube temperature was lowered to 250° C., and then the reaction (fluorination) was started by supplying the reaction tube with hydrogen fluoride at a flow rate of 0.40 g/min and with 1,1,1,3,3-pentachloropropane that had previously been vaporized, at a flow rate of 1.01 g/min, as shown in Table 3. 1 hr after the start of the reaction, the reaction became stable. After that, the reaction products were collected in a manner that is the same as that of Example 9. With this, 66.2 g of an organic matter was obtained. This organic matter was analyzed with a gas chromatograph, and the results of this analysis are shown in Table 4.

EXAMPLES 17–18

In these examples, Example 16 was repeated except in that the reaction temperature was modified as shown Table 3.

What is claimed is:

1. A method for producing 1,1,1,3,3-pentafluoropropane, comprising a step of fluorinating 1-chloro-3,3,3-trifluoropropene in a gas phase by hydrogen fluoride in the presence of a fluorination catalyst, wherein said fluorination catalyst comprises at least one compound of at least one metal selected from the group consisting of aluminum, chromium, manganese, nickel, and cobalt, wherein said at least one compound is selected from the group consisting of oxides, fluorides, chlorides, fluorochlorides, oxyfluorides, oxychlorides, and oxyfluorochlorides.

2. A method according to claim 1, wherein said at least one compound is carried on a carrier.

3. A method according to claim 2, wherein said carrier is at least one selected from the group consisting of aluminum oxides, aluminum fluorides, aluminum chlorides, aluminum fluorochlorides, aluminum oxyfluorides, aluminum oxychlorides, aluminum oxyfluorochlorides, and activated carbon.

4. A method according to claim 2, wherein said at least one compound is in an amount of from 0.1 to 20 wt %, based on a total weight of said carrier.

5. A method according to claim 1, wherein, prior to said step, the fluorination catalyst is treated with a fluorine-containing compound at a temperature that is not lower than a reaction temperature of said step.

6. A method according to claim 5, wherein said fluorine-containing compound is at least one compound selected from the group consisting of hydrogen fluoride, fluorohydrocarbons, and fluorochlorohydrocarbons.

7. A method for producing 1,1,1,3,3-pentafluoropropane, consisting essentially of a step of fluorinating 1-chloro-3,3, 3-trifluoropropene in a gas phase by hydrogen fluoride in the presence of a fluorination catalyst, wherein said fluorination catalyst comprises at least one compound of at least one metal selected from the group consisting of aluminum, chromium, manganese, nickel, and cobalt, wherein said at least one compound is selected from the group consisting of oxides, fluorides, chlorides, fluorochlorides, oxyfluorides, oxychlorides and oxyfluorochlorides.

* * * * *